United States Patent [19]

Fackler

[11] Patent Number: 4,461,284
[45] Date of Patent: Jul. 24, 1984

[54] SURGICAL RETAINING DEVICE

[76] Inventor: Martin L. Fackler, LAIR-CCC, Presidio, San Francisco, Calif. 94129

[21] Appl. No.: 430,648

[22] Filed: Sep. 30, 1982

[51] Int. Cl.³ .............................................. A61B 17/02
[52] U.S. Cl. .................... 128/20; 248/288.5; 269/45; 403/55; 403/56
[58] Field of Search ............... 128/20, 346; 248/288.3, 248/288.5, 481; 403/55, 56, 76, 90; 269/37, 45, 75, 322

[56] References Cited

U.S. PATENT DOCUMENTS

| 1,280,013 | 9/1918 | Goddard | 248/288.5 |
| 1,290,252 | 1/1919 | Lester et al. | 248/481 |
| 1,386,318 | 8/1921 | Cowan | 269/45 |
| 1,446,811 | 2/1923 | Rowland | 269/45 |
| 1,460,697 | 7/1923 | Bendlin | 403/56 |
| 2,561,196 | 7/1951 | Gauthier | 269/37 |
| 3,910,538 | 10/1975 | Baitella | 403/56 |
| 4,143,652 | 3/1979 | Meier et al. | 128/20 |

FOREIGN PATENT DOCUMENTS

| 2717828 | 10/1978 | Fed. Rep. of Germany | 403/55 |
| 608874 | 1/1979 | Fed. Rep. of Germany | 403/55 |

Primary Examiner—Edward M. Coven
Assistant Examiner—Max F. Hindenburg
Attorney, Agent, or Firm—John H. Raubitschek; Neil K. Nydegger; Arthur I. Spechler

[57] ABSTRACT

A retaining device for fixedly holding a surgical instrument in a predetermined spatial orientation during surgery comprising an arm having a ball-and-socket joint for grasping the surgical instrument, another arm having a ball-and-socket joint for securing the device to a stationary base and an intermediate pin joint which connects the arms and acts in conjunction with the ball-and-socket joints to allow placement of the surgical instrument in a desired position. The retaining device further comprised a means at the pin joint for simultaneously tightening all joints of the device after placement of the surgical instrument and thereby fixing the position of the surgical instrument.

6 Claims, 8 Drawing Figures

SURGICAL RETAINING DEVICE

The invention described herein may be manufactured, used and licensed by or for the Government for governmental purposes without the payment of any royalty thereon.

BACKGROUND OF THE INVENTION

This invention relates generally to retaining devices for positioning and holding an object in a desired spatial orientation. More specifically, the invention relates to a device which can be clamped or tightened to hold medical instruments in a stationary position during surgical operations. The present invention is particularly, though not exclusively, useful in a surgical environment where its ease of assembly and disassembly allow it to be quickly cleaned and sterilized between operations.

DESCRIPTION OF THE PRIOR ART

During certain surgical operations it is often necessary to simultaneously use numerous instruments. Frequently, this requires the efforts of several individuals. However, when an instrument need not be moved and can serve its intended purposes in a spatially fixed position, there is no longer a need for the human operator. This fact has been appreciated. Consequently, many devices may be found in the prior art which are specifically designed to retain surgical instruments in a fixed position. The major advantage of such devices are that they reduce the number of persons required to perform the surgery and thereby reduce the economic cost of the operation.

As previously indicated, several retaining devices of varying embodiments are well known in the art. Indeed, the specific embodiment of a ball-and-socket joint to hold the surgical instrument, another ball-and-socket joint for securing the device to a stationary base and an intermediate connecting pin to allow structural cooperation for unrestrained translational and rotational positioning of the surgical instrument is known in the art. For example, the invention disclosed in U.S. Pat. No. 4,143,652 is similar to the present invention insofar as both devices incorporate a single means to simultaneously tighten three joints to obtain rigidity of the device. The single tightening means provides greater ease of operation over other devices in the art which require tightening at more than one point to achieve rigidity. Furthermore, the feature of having a single tightening point helps overcome the problem of shifting which is encountered when subsequent tightening operations cause movement of the surgical instrument from its original intended placement.

Although the present invention can be used in any of the wide variety of tasks which require fixed positioning of objects, such as welding operations or mechanical repairs, the environment where its advantages promise to be most pronounced is in the field of surgical operations. In such operations, a recognized imperative is proper sterilization of surgical equipment. Past practice, using state-of-the-art surgical retaining devices, has been hampered by the difficulties in attaining and maintaining proper sterilization of the devices. These difficulties have, in large part, been due to the mechanical complexity of the prior art devices.

In order to obtain the necessary degrees of spatial freedom required to properly position surgical instruments, prior art retaining devices have typically been very complex in structure. They have comprised numerous parts which have had hidden areas with hard-to-get-at surfaces. Consequently, it has been difficult to disassemble these devices for proper cleaning and sterilization. One attempt to overcome this limitation of structure is through the use of a hood arrangement as suggested in U.S. Pat. No. 4,143,652. Although such a hood can provide some protection for the device from contamination encountered during surgery, it does not provide complete protection. Thus, it does not eliminate the requirement for cleaning and sterilization of the device before its use in a surgical operation. More importantly, it does not overcome the difficulty of dismantling and reassemblying the device which is necessary for such cleaning and sterilization.

SUMMARY OF THE INVENTION

The surgical retaining device of the present invention substantially mitigates the difficulties previously encountered in cleaning and sterilizing such devices by reducing both the number of parts in the device and the complexity of their interconnection. Also, the limited number of joints for tightening and the need for only one tightening point enhance the ability of the device to be rendered rigid and immobile and increase its ease of operation.

In the preferred embodiment of the present invention, two arms are pivotally connected to each other by a pin at one end of the respective arms for relative planar rotation. Each arm, comprises two bars which are connected by a fulcrum attached intermediate the end points of the respective bars to form a pair of tongs. Each pair of tongs, as previously indicated, has one end adapted to receive a pin while the other end is formed with holding surfaces which cooperate as a socket to receive and clamp onto a ball in a manner commonly associated with the familiar ball-and-socket joint.

Operation of the tongs is such that as the end which is adapted to receive the pin is spread, there is a consequent clamping or converging action of the holding surfaces at the opposite end of the tongs. This operation is, of course, reversible so that as the end which is adapted to receive the pin is allowed to converge the clamping action at the opposite end of the tongs is relaxed.

Also included in the preferred embodiment is a means for simultaneous operation of the two pair of tongs through their interconnection at the pin joint. This is achieved by overlapping the ends of the tongs at the pin along the longitudinal axis of the pin so the upper and lower bars of one tongs can urge respectively against the upper and lower bars of the other tongs. In this arrangement, an applied force which simultaneously causes axial displacement along the pin of the upper bar of one tongs and axial displacement along the pin of the lower bar of the other tongs will cause both pairs of tongs to operate in the desired manner. This action will be more easily understood if it is recognized that the preferred embodiment of the present invention further comprises a threaded connection between the pin and the upper bar of one tongs for allowing axial movement of this upper bar relative to the pin during rotation of the pin. Implicit in this motion is the generation of a resultant force between the pin and this upper bar. As the pin is thus turned in the upper bar of one tongs, the structure of the device is such that the pin is made to urge against only the lower bar of the other tongs. Consequently, any increase or decrease in the force applied by the pin and the lower bar it urges against must occur during rotation of the pin. Also, this force must occur simultaneously with, and be equal and opposite to, the force that is generated between the pin and the upper bar of the other tongs during rotation of the pin. Further, these forces are respectively transferred from the upper bar of the one tongs to the upper bar of the other tongs and from the lower bar of the one tongs to the lower bar of the other tongs. In this manner the tongs are operated in concert with each other and both ball-and-socket joints are caused to function simultaneously.

The novel features of this invention, as well as the invention itself, both as to its organization and operation will best be understood from the accompanying drawings, taken in conjunction with the accompanying description, in which similar reference characters refer to similar parts, and in which:

DESCRIPTION OF THE PREFERRED EMBODIMENTS

Figure 1:
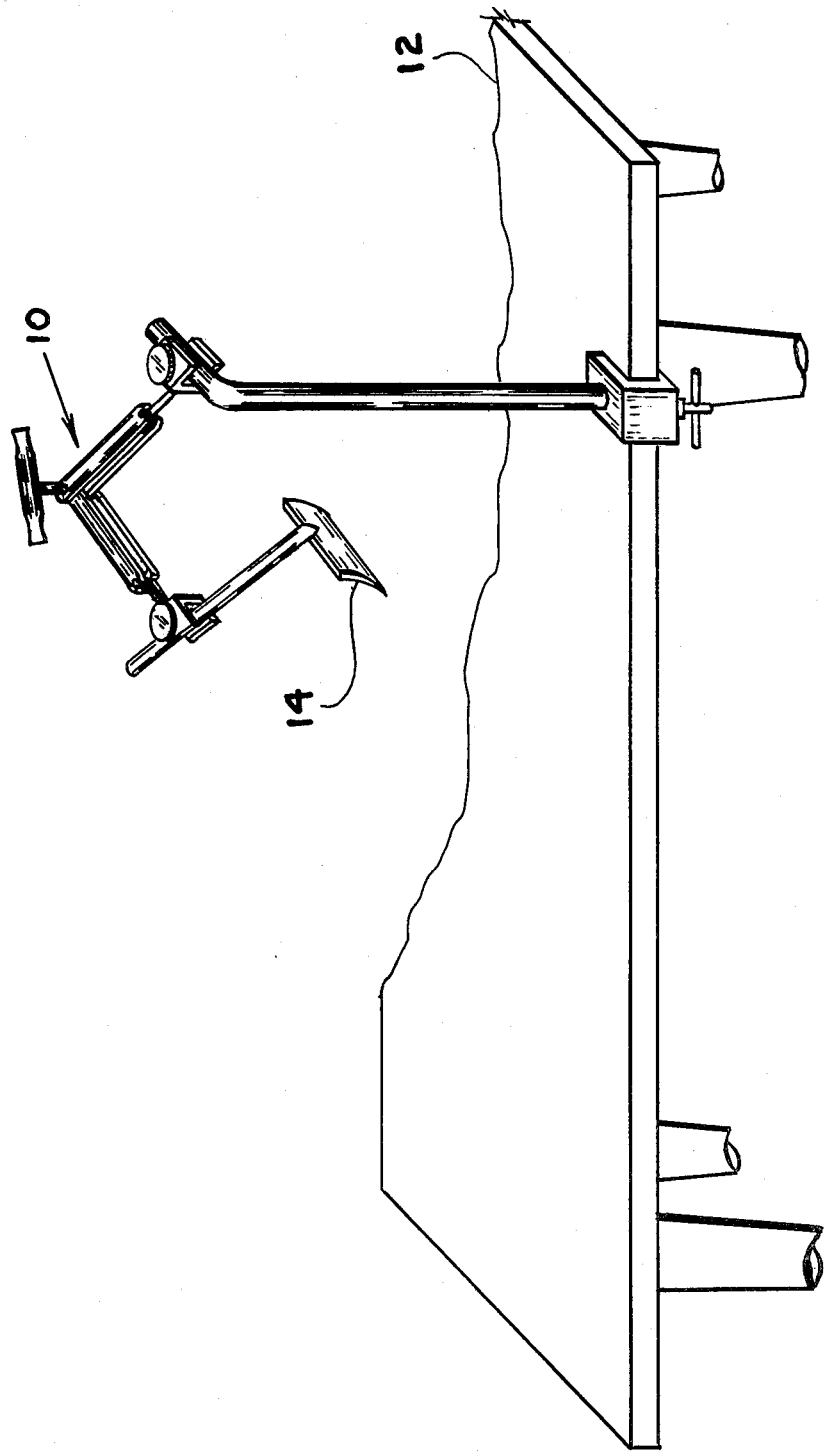
FIG. 1 is a perspective view of the surgical retaining device mounted on an operating table.

The general implementation of the retaining device 10 is best seen in FIG. 1 where it is shown employed for the purpose of retaining, holding or stabilizing an object, such as surgical instrument 14. When used for such purposes, the retaining device 10 functions as a connection between a fixed base or support, such as the operating table 12, and the particular surgical instrument 14 being used. For example, the surgical instrument 14 might be, but need not be limited to, any of the following; a retractor blade, a Balfour bladder blade, a wound hook, sponge forceps, suture holder, or a hemostat. The detailed cooperation of structure employed in the retaining device 10 is best seen in FIG. 2.

Figure 2:
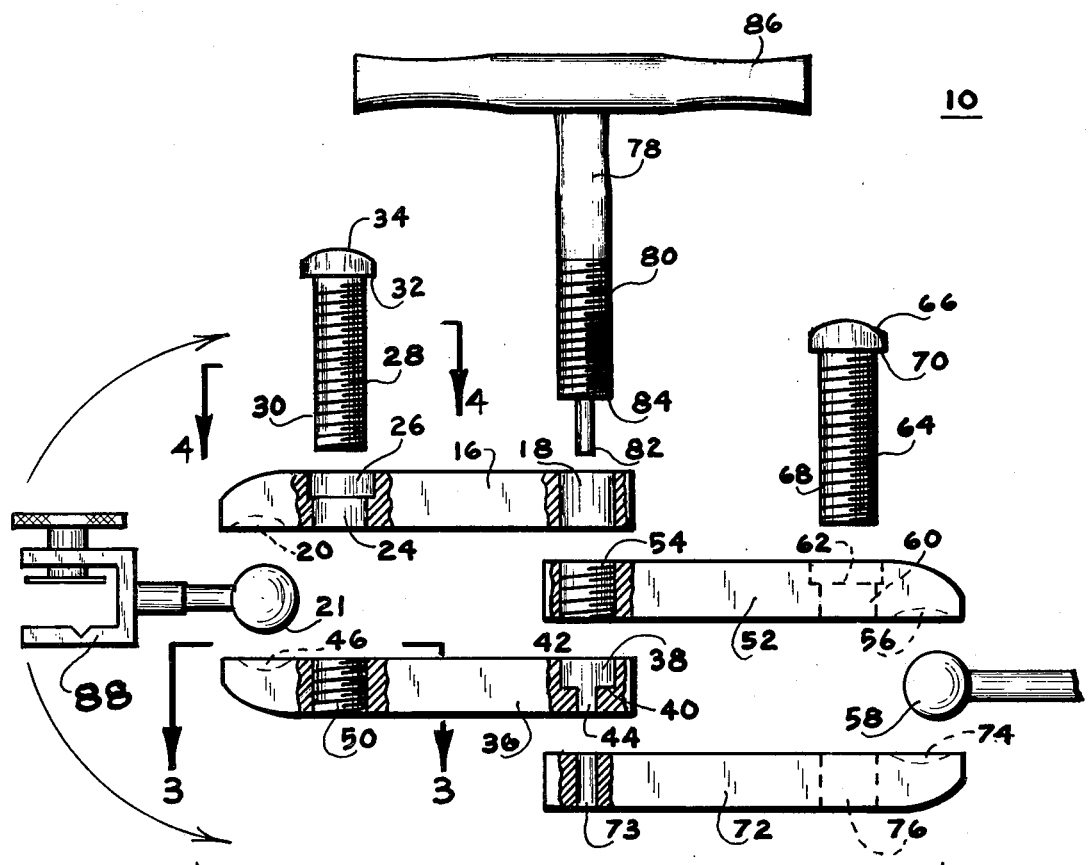
FIG. 2 is an exploded side elevational view of the surgical retaining device with portions broken away and illustrated in sections for the purposes of clarification and illustration.
Figure 4:
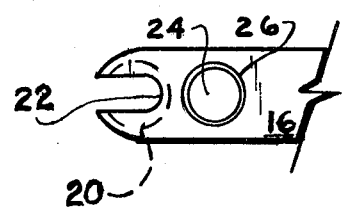
FIG. 4 is a top view of a portion of the device on the line 4—4 of FIG. 2.

Referring now to FIG. 2, it can be seen that the retaining device 10 includes a first upper bar 16 in which there has been formed a smooth-sided channel 18 located near one end of the bar 16. At the other end of first upper bar 16, opposite from channel 18, bar 16 is formed with a depression 20 which is adapted to receive an object, such as the ball 21. As can be best seen in FIG. 4, the end of first upper bar 16, where depression 20 is located, is also formed with an open-ended slot 22 whose length-wise axis is transverse to the axis of channel 18 and which is extended into bar 16 to approximately the midpoint of depression 20. Referring again to FIG. 2, it is seen that intermediate the depression 20 and channel 18, first upper bar 16 also formed with a smooth-sided channel 24 whose axis is substantially parallel to the axis of channel 18. As can be seen in both FIG. 2 and FIG. 4, the diameter of channel 24 is varied to form a shoulder 26 inside channel 24.

Also shown in FIG. 2 is a bolt 28, which is of standard structure and comprises a head 34, a threaded shaft 30, and a lip 32 formed at the juncture of head 34 and shaft 30. In this configuration, bolt 28 is adapted to be received by channel 24 in such a manner that the threaded shaft 30 of bolt 28 can pass through channel 24 until the lip 32 seats against, and is retained by, the shoulder 26 in channel 24.

Figure 3:
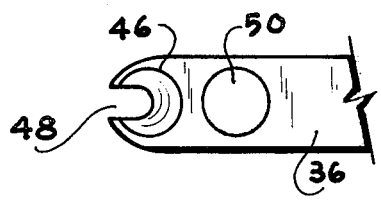
FIG. 3 is a top view of a portion of the device on the line 3—3 of FIG. 2.

Another element of the retaining device 10, also shown in FIG. 2, is a first lower bar 36 which has a smooth-sided channel 38 formed adjacent one of its ends. As illustrated in FIG. 2, the diameter of channel 38 is varied to form a shoulder 40, inside channel 38, which defines the separation between the wide portion 42 and the narrow position 44 of channel 38. It should be noted here that the wide portion 42 of channel 38 is of substantially the same diameter as channel 18 in the first upper bar 16. Adjacent the other end of the first lower bar 36, opposite from channel 38, the first lower bar 36 is formed with a depression 46 which is adapted to receive an object such as the ball 21. As best seen in FIG. 3, the end of the first lower bar 36, where depression 46 is located, is also formed with an open-ended slot 48 whose length wise axis is substantially perpendicular to the axis of channel 38 and which is extended into the first lower bar 36 to approximately the midpoint of depression 46. Referring back to FIG. 2, it is seen that intermediate the depression 46 and channel 38, first lower bar 36 is also formed with a hole 50 which is threaded and adapted to receive the threaded shaft 30 of bolt 28. By this connection bolt 28 can be detachably engaged with first lower bar 36.

Although the preferred embodiment of device 10, as above described, specifically mentions a threaded connection between shaft 30 and the threaded hole 50 of the first lower bar 36, it should be recognized that other means for this connection may be employed. Regardless of the means employed in this connection it is important that bolt 28 be adapted to extend through channel 24 in the first upper bar 16 until lip 32 seats on shoulder 26 before shaft 30 of bolt 28 is detachably engaged into hole 50 in the first lower bar 36. A threaded connection between bolt 28 and first lower bar 36. is particularly suitable for device 10 because, after bolt 28 is received into hole 50, such a connection will allow for adjustments in the distance of lip 32, on bolt 28, from the first lower bar 36. As will be appreciated more fully later, the ability to vary this distance will provide for greater versatility in grasping objects.

Still another element of the device 10, as seen in FIG. 2, is a second upper bar 52. A channel 54, having threaded sides, is formed adjacent one end of the second upper bar 52. Adjacent the opposite end of second upper bar 52 a depression 56 is formed which is adapted to receive an object such as the ball 58. Intermediate the depression 56 and the channel 54, the second upper bar 52 is formed with a smooth-sided channel 60 whose axis is generally parallel to the axis of channel 54. As can also be seen in FIG. 2, the diameter of channel 60 is varied to form a shoulder 62 inside the channel 60.

FIG. 2 also shows a bolt 64 which, like bolt 28, is of standard structure and comprises a head 66, a threaded shaft 68 and a lip 70 formed at the juncture of head 66 and shaft 68. In this configuration bolt 64 is adapted to be received by channel 60 in such a manner that the threaded shaft 68 can pass through channel 60 until the lip 70 of head 66 seats against, and is retained by, the shoulder 62 is channel 60.

At this point it should be recognized that, in an alternate embodiment of the retaining device 10, the channel 60 of second upper bar 52 can be formed without shoulder 62. In this case, bolt 64 is adapted to allow threaded shaft 68 to pass through channel 60 until lip 70 seats against, and is retained by, the surface of second upper bar 52. In a similar manner, shoulder 26 in channel 24 of first upper bar 16 can be eliminated. Bolt 28 would then be adapted to allow threaded shaft 30 to pass through channel 24 until lip 32 seats against, and is retained by, the surface of first upper bar 16.

Still referring to FIG. 2, it can be seen that a second lower bar 72 is also an element of the retaining device 10. Adjacent one end of second lower bar 72 is a smooth-sided channel 73 whose diameter is substantially the same as the diameter of narrow portion 44 of channel 38 in first lower bar 36. Adjacent the other end of second lower bar 72 is a depression 74 which is adapted to receive an object such as the ball 58. Intermediate depression 74 and channel 73, on second lower bar 72, is a threaded hole 76 which is adapted to receive the threaded shaft 68 of bolt 64. By this connection, bolt 64 can be attachably engaged with second lower bar 72. For reasons similar to those previously discussed with regard to the engagement of bolt 28 with hole 50, the threaded engagement of bolt 64 with hole 76 is only a preferred embodiment. Other means of engagement may also be used.

A pin 78, as shown in FIG. 2, is an essential element of the retaining device 10. Part of pin 78 is a threaded rod 80 whose diameter is adapted to allow its passage through the channel 18 in first upper bar 16. Threaded rod 80 is also adapted to screwably engage with the threads of channel 54 in second upper bar 52. An integral part of pin 78 is a stem 82 which is coaxial with rod 80 and is located on pin 78 to form an abutment 84 at the juncture of stem 82 and rod 80. The diameter of stem 82 is such that it can pass into and through the narrow portion 44 of channel 38 in first lower bar 36 and into channel 73 in second lower bar 72 until the abutment 84 seats against and is retained by the shoulder 40 in channel 38 of first lower bar 36. Pin 78 also includes some means, such as a handle 86, by which the pin 78 can be rotated to screw the threaded portion of rod 80 into the threaded channel 54. A handle 86, such as the one shown in FIG. 2, is particularly suited for manual rotation of pin 78.

Figure 8:
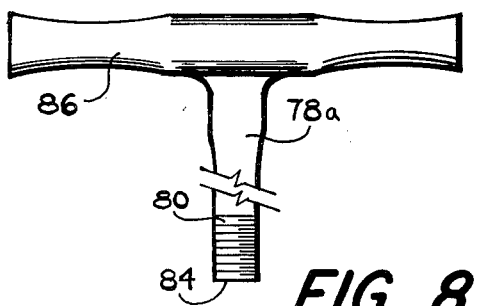
FIG. 8 is a side view of a part of the surgical retaining device shown in FIG. 5.
Figure 5:
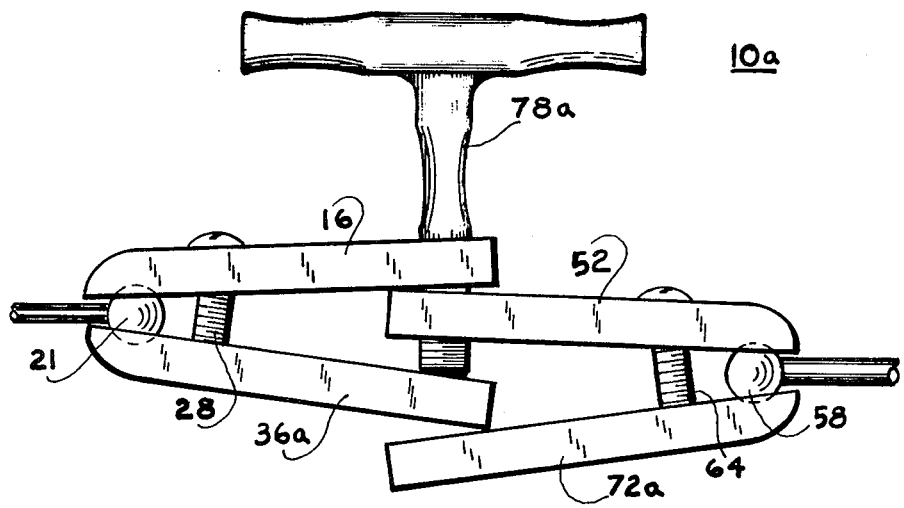
FIG. 5 is a side elevational view of an alternate embodiment of the surgical retaining device showing a slightly exagerated alignment of its parts in the clamped position.
Figure 6:
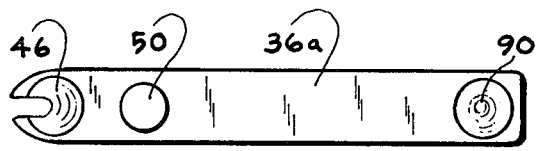
FIG. 6 and FIG. 7 are top views of parts of the surgical retaining device shown in FIG. 5.
Figure 7:
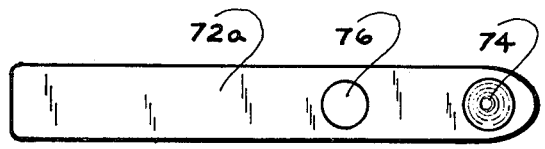

An alternate embodiment of the surgical retaining device 10 is shown in FIG. 5 as a modified retaining device 10a. In order to best understand the differences between the structures of the retaining device 10 shown in FIG. 2 and the modified retaining device 10a shown in FIG. 5, reference should be first made back to FIG. 2. As will be discussed, only the pin 78, the first lower bar 36, and the second lower bar 72, all of which are shown in FIG. 2, need be changed for construction of the modified retaining device 10a. To discuss each of these modified parts separately, attention is first directed to the modified pin 78a shown in FIG. 8. Modified pin 78a in FIG. 8 is similar to the pin 78 shown in FIG. 2 with the exception that the stem 82 which is attached to pin 78 has been eliminated. The next modification can be appreciated by comparing the first lower bar 36, as shown in FIG. 2 with the modified first lower bar 36a, shown in FIG. 6. For the modified first lower bar 36a the channel 38 and narrow portion 44 which were formed in first lower bar 36 have been eliminated. Instead, modified first lower bar 36a is formed with a depression 90 which is adopted to receive abutment 84 of modified pin 78a and which is on the same side of modified first lower bar 36 as depression 46 but at the opposite end therefrom. It should be noted here that depression 90 itself may be eliminated. The last comparison, necessary for an understanding of the modified retaining device 10 a, is made between the second lower bar 72 shown in FIG. 2 and the modified second lower bar 72a shown in FIG. 7. As seen in FIG. 7, modified second lower bar 72a does not have the channel 73 which is found in second lower bar 72. In all other respects, modified second lower bar 72a and second lower bar 72 are substantially the same. The cooperation of structure for modified pin 78a, modified first lower bar 36a and modified second lower bar 72a in modified retaining device 10a is substantially similar to the cooperation of structure for the respective elements as discussed for retaining device 10. Unless specifically noted otherwise, the discussion of retaining device 10 is applicable in all essential respects to modified retaining device 10a.

Before leaving the description of the preferred embodiments and proceeding to the operation of device 10 it is necessary to recognize that in the above descriptions of the device 10, a very close tolerance between certain elements may be detrimental to their operation and interaction. More specifically, in the preferred embodiment, channel 24 in first upper bar 16 should be oversized to allow easy passage of bolt 28 through channel 24 and to subsequently allow some general motion of bolt 28 within channel 24 when device 10 is untightened. Similarly, channel 18 in first upper bar 16, channel 38 in first lower bar 36 and channel 73 in second lower bar 72 should be oversized to allow easy passage of pin 78 through the respective channels and to subsequently allow some general motion of pin 78 within the channels when device 10 is untightened. Also, channel 60 in second upper bar 52 should be oversized with respect to bolt 64 for these same purposes. On the other hand, the threaded connection between bolt 28 and hole 50 in first lower bar 36, the threaded correction between pin 78 and channel 54 in second upper bar 52 and the threaded connection between bolt 64 and hole 76 in second lower bar 72, should not allow for excessive play when device 10 is either tightened or untightened.

Since the ease of assembly and disassembly is considered a major feature of the present invention, operation of the device 10 will be best understood by starting with the device 10 disassembled into its constituent elements. Device 10 is assembled in the following general manner. It should be noted, however, that the precise sequence of assembly is not as important as is the ultimate cooperation of the elements. Several effective variations in the following sequence are obvious. A suggested sequence for assembly is to pass bolt 28 through the channel 24 in first upper bolt 16 and screw the threaded shaft 30 of bolt 28 into the threaded hole 50 in first lower bar 36. First upper bar 16 can then be aligned with first lower bar 36 to form a subassembly which can function as a pair of tongs wherein the first upper bar 16 and the first lower bar 36 are the arms and the bolt 28 is the fulcrum of the tongs. Also, FIG. 2 shows that in the above described orientation, depression 20 in first upper bar 16 faces depression 46 in first lower bar 36 for simultaneous adaptation to the opposite sides of an object, such as the ball 21, to form a ball-and-socket joint.

Similarly, a second pair of tongs can be formed by the second upper bar 52, the second lower bar 72, and the bolt 64. In this subassembly, bolt 64 is passed through channel 60 in second upper bar 52 and then the threaded shaft 68 of bolt 64 is screwed into the threaded hole 76 in second lower bar 72. Second upper bar 52 is then aligned with second lower bar 72 to form a pair of tongs wherein the second upper bar 52 and the second lower bar 72 are the arms and bolt 64 is the fulcrum of the tongs. In this orientation, depression 56 in second upper bar 52 faces depression 74 in second lower bar 72 for adaptation to the opposite sides of an object, such as the ball 58, to form a ball-and-socket joint.

Both pairs of tongs, as previously described, are now placed so that channel 18 of first upper bar 16, channel 54 of second upper bar 52, channel 38 of first lower bar 36, and channel 73 of second lower bar 72 are coaxially aligned in the order stated here and as shown in FIG. 2. Pin 78 is now used to connect one pair of tongs with the other. To do this, stem 82 and rod 80 of pin 78 are passed through channel 18 of first upper bar 16 until the threads of rod 80 make contact and engage with the threads in channel 54 of second upper bar 52. Pin 78 is then rotated to screw rod 80 into channel 54 and allow advancement of pin 78 through channel 54. As pin 78 is so advanced, it will be important to sequentially guide stem 82 into the narrow portion 44 of channel 38 in first lower bar 36 and into channel 73 of second lower bar 72. Advancement of pin 78 should be continued in the above manner until abutment 84 urges against shoulder 40 in channel 38 of first lower bar 36.

As an aside, it should be noted that in an alternate embodiment of device 10, channel 38 can be formed having no variation in its diameter. Thus, shoulder 40 is eliminated. In this alternate embodiment the diameter of channel 38 would be adapted to receive only stem 82 of pin 78 and not rod 80. Abutment 84, after being advanced through channel 54, would then rest on and urge against the surface of first lower bar 36 rather than against a shoulder 40 as described in the preferred embodiment.

For the previously discussed alternate embodiment shown in FIG. 5, pin 78a is rotated to screw rod 80 into channel 54 until abutment 84 sets into depression 90 and thereafter urges against modified first lower bar 36a. In turn, and as a consequence of the urging of pin 78a against first lower bar 36a, first lower bar 36a urges against second lower bar 72a.

Device 10 is now assembled. However, before it is used for its intended purposes the surgical instrument 14 needs to be fitted with an extension, such as ball 21 (FIG. 2), which can be grasped by the device 10. Any means, such as the clamp 88 shown in FIG. 2, which can be fixedly secured to the instrument 14 will suffice for this purpose. Likewise, a fixed base, such as the operating table 12 shown in FIG. 1, needs to be fitted with an extension, such as ball 58 (FIG. 2), which can be grasped by the device 10.

Once the above described extensions are in place, device 10 can be employed to orient and stabilize the surgical instrument 14 relative to the operating table 12. To do this, ball 21 is placed between depression 20 in first upper bar 16 and depression 46 in first lower bar 36. Pin 78 is then rotated. This rotation, as discussed above, will cause pin 78 to advance through channel 54 of second upper bar 52 and to urge abutment 84 of pin 78 against shoulder 40 in channel 38 of first lower bar 36. The consequence of this rotation is creation of a force against first lower bar 36 at the shoulder 40 and an equal and opposite force against second upper bar 52 on the threads in channel 54. As a result, the end of second upper bar 52 where channel 54 is located will move away from the end of first lower bar 36 where shoulder 40 is located. Also, the end of second upper bar 52 urges against the end of first upper bar 16 where channel 18 is located and causes this end to move away from the end of first lower bar 36 where shoulder 40 is located. Simultaneously, the end of first lower bar 36 urges against the end of second lower bar 72 where channel 73 is located and causes this end to move away from the end of second upper bar 52 where channel 54 is located. Thus, by rotation of pin 78 the ends of first upper bar 16 and first lower bar 36, which are engaged with pin 78, can be caused to diverge. At the same time, the ends of second upper bar 52 and second lower bar 72, which are engaged with pin 78, are caused to diverge. As this action proceeds, bolt 28 acts as a fulcrum and causes convergence of the ends of first upper bar 16 and first lower bar 36 where, respectively, depression 20 and depression 46 are located. This convergence is continued, as a result of the rotation of pin 78, until depression 20 and depression 46 adapt to and grasp the ball 21 to form a ball-and-socket joint. It should be noted that the convergence of depression 20 and depression 46 can also be controlled through adjustment of bolt 28 relative first lower bar 36 to change the length of the fulcrum to account for variations in the sizes of ball 21.

Either after the ball 21 is grasped by device 10, or simultaneously with the grasping of ball 21, the device 10 can be made to grasp the ball 58 in a similar manner and through an action similar to that described above. Thus, a ball-and-socket joint can be formed with the adaptation to and grasping of a ball 58 between the depression 56 in second upper bar 52 and the depression 74 in second lower bar 72. Again, changes in the length of the fulcrum through the adjustment of bolt 64 relative to second lower bar 72, can account for variations in the size of ball 58.

Once device 10 is grasping both ball 21 and ball 58, the entire combination can be tightened by further rotation of pin 78 until the desired degree of rigidity is achieved. Similarly the device 10 can be loosened by a counter rotation of the pin 78. When loosened, the surgical instrument 14 can be reoriented and, if desired, the device 10 can again be made rigid by rotation of the pin 78.

After device 10 has performed its desired function it can be disassembled by reversing the steps set forth above for assembly. Dissembled, device 10 can be cleaned and sterilized prior to reassembly and subsequent use.

I claim:

1. A device for holding an object in a predetermined orientation relative to a fixed support comprising:
   a rod,
   a stem having a smaller diameter than said rod and coaxially integral with one end of said rod to form an abutment at the juncture of said stem with said rod,
   a first upper bar having one end slidably associated with said rod and formed with a depression at its opposite end for engaging a portion of said object,
   a second upper bar having one end operatively associated with said rod on said rod intermediate said first upper bar and said abutment and formed with a depression at it opposite end for engaging a portion of said support, a first lower bar having one end slidably associated with said stem to allow said abutment to urge against said first lower bar and formed with a depression at its opposite end for engaging another portion of said object, a second lower bar having one end slidably associated with said stem to place said first lower bar intermediate said second upper bar and said second lower bar and formed with a depression at its opposite end for engaging another portion of said support, a first fulcrum operatively engaged with said first upper bar intermediate said ends of said first upper bar and detachably engaged with said first lower bar intermediate said ends of said first lower bar, a second fulcrum operatively engaged with said second upper bar intermediate said ends of said second upper bar and detachably engaged with said second lower bar intermediate said ends of said second lower bar, and means associated with said rod for urging said abutment against said first lower bar to separate said ends of said first and second lower bars at said stem from said ends of said first and second upper bars located at said rod and to cause said opposite ends of said bars to converge and respectively grasp said object and said support.

2. A device as cited in claim 1 wherein said means associated with said rod for urging said abutment against said first lower bar comprises:

a connection wherein said rod is threadably engaged with said second upper bar for allowing motion of said rod relative to said second upper bar upon rotation of said rod, and means for rotating said rod.

3. A device as cited in claim 2 wherein said means for rotating said rod comprises:

a handle attached to said rod and adapted for manual rotation of said rod.

4. A device as cited in claim 3 further comprising:

a first ball adapted for attachment to said object and engagable with said depression in said first upper bar and said depression in said first lower bar to form a ball-and-socket joint.

5. A device as cited in claim 4 further comprising:

a second ball adapted for attachment to said support and engagable with said depression in said second upper bar and said depression in said second lower bar to form a ball-and-socket joint.

6. A device for holding an object in an predetermined orientation relative to a fixed support comprising:

a rod having an abutment at one end, a first upper bar having one end slidably associated with said rod and formed with a depression at its opposite end for engaging a portion of said object, a second upper bar having one end operatively associated with said rod on said rod intermediate said first upper bar and said abutment and formed with a depression at its opposite end for engaging another portion of said support, a first lower bar having one end associated with said rod to allow said abutment on said rod to urge against said first lower bar and formed with a depression at its opposite end for engaging a portion of said object, a second lower bar having one end associated with said first lower bar to place said first lower bar intermediate said second upper bar and said second lower bar and formed with a depression at its opposite end for engaging another portion of said support, a first fulcrum operatively engaged with said first upper bar intermediate said ends of said first upper bar and detachably engaged with said first lower bar intermediate said ends of said first lower bar, a second fulcrum operatively engaged with said second upper bar intermediate said ends of said second upper bar and detachably engaged with said second lower bar intermediate said ends of said second lower bar, and means associated with said rod for urging said abutment against said first lower bar to separate said ends of said first and second lower bars opposite said depressions from said ends of said first and second upper bars opposite said depressions and to cause said opposite ends of said bars to converge and respectively grasp said object and said support.

* * * * *